US010420598B2

(12) United States Patent
Mirza et al.

(10) Patent No.: US 10,420,598 B2
(45) Date of Patent: Sep. 24, 2019

(54) DEVICE FOR DRIVING FIXATION ELEMENTS INTO BONE AND METHOD OF USE THEREOF

(71) Applicant: A.M. SURGICAL, INC., Smithtown, NY (US)

(72) Inventors: Ather Mirza, Smithtown, NY (US); Romi Mirza, Smithtown, NY (US)

(73) Assignee: A.M. SURGICAL, INC., Smithtown, NY (US)

( * ) Notice: Subject to any disclaimer, the term of this patent is extended or adjusted under 35 U.S.C. 154(b) by 0 days.

(21) Appl. No.: 15/837,910

(22) Filed: Dec. 11, 2017

(65) Prior Publication Data

US 2018/0360519 A1 Dec. 20, 2018

Related U.S. Application Data

(63) Continuation of application No. 14/644,838, filed on Mar. 11, 2015, now Pat. No. 9,867,647.

(Continued)

(51) Int. Cl.
| | | |
|---|---|---|
| *A61B 17/92* | (2006.01) | |
| *A61B 17/04* | (2006.01) | |
| *A61B 17/72* | (2006.01) | |
| *A61B 17/84* | (2006.01) | |
| *A61B 17/56* | (2006.01) | |
| *A61B 17/00* | (2006.01) | |

(52) U.S. Cl.
CPC .......... *A61B 17/92* (2013.01); *A61B 17/0401* (2013.01); *A61B 17/72* (2013.01); *A61B 17/848* (2013.01); *A61B 17/921* (2013.01); *A61B 2017/00544* (2013.01); *A61B 2017/00548* (2013.01); *A61B 2017/0409* (2013.01); *A61B 2017/564* (2013.01); *A61B 2017/924* (2013.01)

(58) Field of Classification Search
CPC . A61B 17/0401; A61B 17/0642; A61B 17/68; A61B 17/72; A61B 17/846; A61B 17/848; A61B 17/92; A61B 17/921; A61B 2017/548; A61B 2017/564; A61B 2017/00544; A61B 2017/0647; A61B 2017/922; A61B 2017/924; A61B 2017/00548; B25B 21/023
See application file for complete search history.

(56) References Cited

U.S. PATENT DOCUMENTS 3,219,022 A * 11/1965 Hagemeyer ...... A61B 17/12022
124/61
3,602,218 A * 8/1971 Riordan ................. A61B 17/68
206/363

(Continued)

FOREIGN PATENT DOCUMENTS

WO 2009/109198 9/2009

OTHER PUBLICATIONS

File history of U.S. Appl. No. 14/644,838, filed Mar. 11, 2015.

*Primary Examiner* — Eduardo C Robert
*Assistant Examiner* — Steven J Cotroneo
(74) *Attorney, Agent, or Firm* — Ping Wang; Morris, Manning & Martin, LLP

(57) ABSTRACT

A implanting device for driving a fastener or fixation element into bone is described. Also described are methods for using a implanting device for driving a fastener or fixation element into bone and a kit comprising a pneumatic implanting device for driving a fastener or fixation element into bone.

27 Claims, 1 Drawing Sheet

Related U.S. Application Data

(60) Provisional application No. 62/051,094, filed on Sep. 16, 2014.

(56) References Cited

U.S. PATENT DOCUMENTS

| | | | | |
|---|---|---|---|---|
| 4,050,528 | A | * | 9/1977 | Foltz .................. A61B 17/1628 173/170 |
| 4,450,835 | A | * | 5/1984 | Asnis ................. A61B 17/1721 606/65 |
| 5,485,887 | A | | 1/1996 | Mandanis |
| 5,487,499 | A | * | 1/1996 | Sorrentino ....... A61B 17/07207 173/20 |
| 6,019,761 | A | | 2/2000 | Gustilo |
| 6,578,565 | B2 | * | 6/2003 | Casas Salva ........... F41B 11/54 124/40 |
| 7,131,503 | B2 | * | 11/2006 | Furuta .................... B25B 21/00 173/48 |
| 7,481,347 | B2 | * | 1/2009 | Roy ..................... A61B 17/072 227/175.1 |
| 8,485,412 | B2 | * | 7/2013 | Shelton, IV ....... A61B 17/0644 227/175.1 |
| 9,867,647 | B2 | * | 1/2018 | Mirza .................... A61B 17/92 |
| 2007/0219565 | A1 | | 9/2007 | Saadat |
| 2009/0275946 | A1 | * | 11/2009 | Duncan .............. A61B 17/1725 606/62 |
| 2010/0305624 | A1 | * | 12/2010 | Lozier ................. A61B 17/068 606/86 R |
| 2013/0204264 | A1 | * | 8/2013 | Mani .................... A61F 2/4607 606/99 |

\* cited by examiner

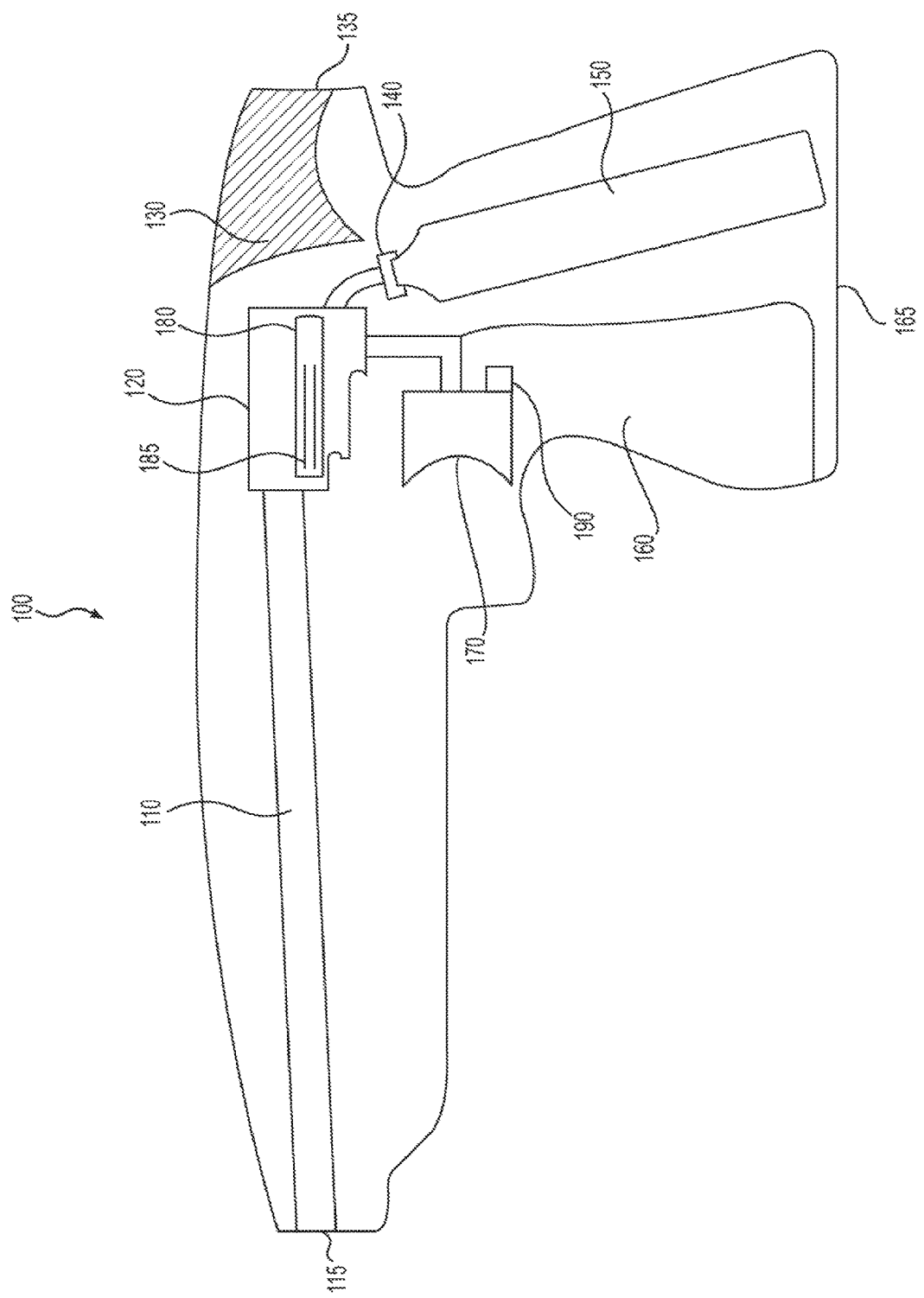

DEVICE FOR DRIVING FIXATION ELEMENTS INTO BONE AND METHOD OF USE THEREOF

This application is a continuation application of U.S. patent application Ser. No. 14/644,838, filed Mar. 11, 2015, which claims the priority of U.S. Provisional Application Ser. No. 62/051,094, filed Sep. 16, 2014. The entirety of the aforementioned application is incorporated herein by reference.

FIELD

This application generally relates to medical devices. In particular, the application relates to a device for implanting fixtures into bone.

BACKGROUND

Complex and simple fractures of bones have been found to heal more quickly and efficiently when the fragments are held together with fixation elements such as Kirschner wires (k-wires) or intramedullary nails (IM nails). However, at times it can be difficult to insert fixation elements into the bone quickly enough or with sufficient force in order to make effective contact between the bone fragments in a reduced fracture.

The present application provides a device for effectively and rapidly driving fasteners and fixation elements into bone tissue using pneumatic pressure.

One aspect of the present application relates to an implanting device for driving a fastener or fixation element into bone, comprising: a chamber for holding at least one fastener or fixation element, a barrel having a proximal end and a distal end, wherein said proximal end is connected to said chamber for propelling said fastener or fixation element from said chamber, a propulsion source functionally connected to said chamber, and a triggering mechanism for releasing propellant from said propulsion source into said chamber and charging said chamber in order to propel said fastener or fixation element from said chamber through said barrel and driving said fastener or fixation element into bone contacted with said distal end.

Another aspect of the present application relates to a pneumatic implanting device for driving a fastener or fixation element into bone, comprising: a chamber for holding at least one fastener or fixation element, a barrel having a proximal end and a distal end, wherein said proximal end is connected to said chamber for propelling said fastener or fixation element from said chamber, a gas source functionally connected to said chamber, and a triggering mechanism for releasing propellant gas from said gas source into said chamber and charging said chamber in order to propel said fastener or fixation element from said chamber through said barrel and driving said fastener or fixation element into bone contacted with said distal end.

Another aspect of the present application relates to a method for the fixation of a fractured long bone with an intramedullary nail, comprising: providing an access point to the medullary canal of said long bone, reducing the bone fragments at the fracture, contacting the distal end of the barrel of an implanting device for driving a fastener or fixation element into bone with said access point, aligning the barrel of said device with said medullary canal at said access point, and actuating the trigger mechanism of said implanting device to deliver an IM nail into said medullary canal, thereby fixing said bone fragments in said reduced state, wherein said implanting device for driving a fastener or fixation element into bone comprises: a chamber for holding at least one fastener or fixation element, a barrel having a proximal end and a distal end, wherein said proximal end is connected to said chamber for propelling said fastener or fixation element from said chamber, a propellant source functionally connected to said chamber, and a triggering mechanism for releasing propellant from said propellant source into said chamber and charging said chamber in order to propel said fastener or fixation element from said chamber through said barrel and driving said fastener or fixation element into bone contacted with said distal end.

Still another aspect of the present application relates to a method for the fixation a fractured bone using at least one k-wire, comprising: reducing at least one bone fragment with at least one adjacent fragment or the main body of the bone, contacting the distal end of the barrel of an implanting device for driving a fastener or fixation element into bone with said at least one bone fragment, said at least one adjacent fragment or said main body of the bone, aligning the implanting device with said at least one bone fragment and said at least one adjacent fragment or said main body of the bone, and actuating the trigger mechanism of said implanting device to deliver a k-wire affixing said at least one bone fragment to said at least one adjacent fragment or the main body of the bone, thereby fixing said at least one bone fragment in said reduced state, wherein said implanting device for driving a fastener or fixation element into bone comprises: a chamber for holding at least one fastener or fixation element, a barrel having a proximal end and a distal end, wherein said proximal end is connected to said chamber for propelling said fastener or fixation element from said chamber, a propulsion source functionally connected to said chamber, and a triggering mechanism for releasing propellant from said propulsion source into said chamber and charging said chamber in order to propel said fastener or fixation element from said chamber through said barrel and driving said fastener or fixation element into bone contacted with said distal end.

Yet another aspect of the present application relates to a kit comprising an implanting device for driving a fastener or fixation element into bone and a fastener or fixation element, wherein said implanting device for driving a fastener or fixation element into bone comprises: a chamber for holding at least one fastener or fixation element, a barrel having a proximal end and a distal end, wherein said proximal end is connected to said chamber for propelling said fastener or fixation element from said chamber, a propellant source functionally connected to said chamber, and a triggering mechanism for releasing propellant from said propellant source into said chamber and charging said chamber in order to propel said fastener or fixation element from said chamber through said barrel and driving said fastener or fixation element into bone contacted with said distal end.

BRIEF DESCRIPTION OF THE DRAWINGS

The accompanying drawings illustrate one or more embodiments of the present application and, together with the written description, serve to explain the principles of exemplary embodiments of the present application.

FIG. 1 shows an embodiment of the device of the present application.

DETAILED DESCRIPTION

The following detailed description is presented to enable any person skilled in the art to make and use the device. For purposes of explanation, specific nomenclature is set forth to provide a thorough understanding of the present device and methods. However, it will be apparent to one skilled in the art that these specific details are not required to practice the making or use of the device. Descriptions of specific applications are provided only as representative examples. The present device and methods are not intended to be limited to the embodiments shown, but is to be accorded the widest possible scope consistent with the principles and features disclosed herein.

One aspect of the present application relates to an implanting device for inserting fasteners and fixation elements into a bone. The present device propels a projectile in order to introduce a fixation implant into a bone, either in a percutaneous or in an open (exposed bone) manner.

As used herein, "reduction," "reduced" and "reducing" refer to a medical procedure to restore a fracture to the correct alignment by moving the fragments into contact with one another in the correct position for bone healing.

A "fastener," as used herein, refers to an element that partially embeds into bone or hard tissue to fasten or anchor ligament, tendon or suture material to the bone. Examples of fasteners include, but are not limited to suture anchors, pins, screws and staples. Fasteners of the present application can be composed of metal, plastic, bioabsorbable material, ceramic, other suitable material or combinations thereof.

A "fixation element," as used herein, refers to an element that completely partially embeds into bone, bone fragments or hard tissue to fasten in order to immobilize reduced bone fragments in a position where the fragments can grow together. Examples of fixation elements include, but are not limited to k-wires and IM nails. Fixation elements of the present application can be composed of any suitable biocompatible material including, but not limited to, metal alloys, plastic, bioabsorbable material, ceramic, or combinations thereof.

The device of the present application can be used to drive fasteners or fixation elements into and immobilize fragments of any fractured bone in a mammalian body. In a particular embodiment, said mammal is a human.

In particular embodiments, the bone is a long bone, having a shaft and two extremities. Long bones are found in the limbs and include the clavicle, humerus, radius, ulna, femur, tibia, fibula, metacarpal and metatarsal bones, including the phalanges.

As used herein, the "proximal" end of a long bone refers to the extremity of the bone closest to the center of the body when the limb is extended. As used herein, the "distal" end of a long bone refers to the extremity of the bone farthest from the center of the body when the limb is extended. The device of the present application may be used to immobilize the fragments of a fracture at the proximal end of a long bone, the distal end of a long bone, or the shaft of a long bone, or a combination thereof.

As used herein, the "proximal" end of a device, or a part of a device, is the end that is towards the practitioner holding or operating the device. As used herein, the "distal" end of a device, or a part of a device, is the end that is towards the subject into whom a fastener is to be delivered.

As used herein, the "distal" end of a fastener is the end of the fastener that is oriented towards the subject into whom the fastener is to be delivered, i.e., the end of the fastener that makes the initial contact with the bodily tissue of the subject. As used herein, the "proximal" end of a fastener is the end of the fastener that is opposite the "distal" end of the fastener.

In other particular embodiments, the device of the present application can be used to immobilize the fragments of a fractured short bone, including the patella, sesamoid, carpal and tarsal bones.

In further particular embodiments, the device of the present application can be used to immobilize the fragments of a fractured flat bone, including the skull, cranium, occipital, parietal, frontal, nasal, lachrymal, vomer, scapula, os innominatum, sternum, and rib bones.

In additional particular embodiments, the device of the present application can be used to immobilize the fragments of a fractured irregular bone, including the vertebrae, sacrum, coccyx, temporal, sphenoid, ethmoid, malar, superior maxillary, inferior maxillary, palate, inferior turbinated, and hyoid bones.

One aspect of the present application relates to a pneumatic implanting device for driving a fastener or fixation element into bone. The device comprises a chamber for holding at least one fastener or fixation element, a barrel having a proximal end and a distal end, wherein said barrel is for the delivery of the fastener or fixation element into bone, and a triggering mechanism for releasing a propulsion source.

In some embodiments, said fastener or fixation element is selected from the group consisting of a Kirschner wire (k-wire), an intramedullary mail (IM nail) or a suture anchor.

In one embodiment of the device, said proximal end of the barrel is connected to said for propelling said fastener or fixation element from said chamber, a propulsion source functionally connected to said chamber, and a triggering mechanism for releasing propellant from said propulsion source into said chamber and charging said chamber in order to propel said fastener or fixation element from said chamber through said barrel and driving said fastener or fixation element into bone contacted with said distal end.

In another embodiment, the device further comprises a replaceable cartridge for containing said at least one fastener or fixation element in said chamber. In a further embodiment, said cartridge is disposable. In another further embodiment, said cartridge contains more than one fastener or fixation element.

In another embodiment, said propellant is a gas and said propulsion source is a gas source. In some further embodiments, said gas source is a tube that connects to an external gas supply. In yet another further embodiment, said gas source is a replaceable canister of compressed gas. In a related embodiment, said compressed gas is medical grade air.

In still another embodiment, said propulsion source is an explosive material and said propellant is the explosion of said explosive material.

In particular embodiments, the device comprises a piston for propelling a fastener or fixation element from the chamber, through the barrel from the proximal to the distal end and into the bone. In some embodiments, the piston has a proximal and a distal end and the distal end comprises a concave depression, cup, slot or other female-type feature into which the proximal end of the fastener or fixation element inserts or locates in order to secure and/or center the fastener or fixation element against the piston. In some embodiments, the pressure of the propellant builds up proximal to the piston in order to propel said piston in a distal direction when the triggering mechanism is actuated.

In further embodiments, the piston comprises a retainer mechanism that prevents the piston from exiting the distal end of the barrel. In other embodiments, the piston is shaped such that the distal-most portion thereof protrudes from the barrel upon delivery of the fastener or fixation element into bone.

In other particular embodiments, the device lacks a piston, wherein the fastener or fixation element fits into the barrel in such a manner that the propellant is contained in contact with and proximal to the fastener or fixation element. Upon actuation of the triggering mechanism, said propellant drives said fastener or fixation element in a proximal to distal direction down the barrel into bone.

In another embodiment of the device, the device comprises a compressed or loaded spring located proximal to said chamber as a propulsion source and the release of the spring from compression or loading is the propellant for driving said at least one fastener or fixation element through said barrel into bone. In particular embodiments, the device comprising a compressed or loaded spring further comprises a piston for propelling a fastener or fixation element from the chamber, through the barrel from the proximal to the distal end and into the bone. In some embodiments, the piston has a proximal and a distal end and the distal end comprises a concave depression, cup, slot or other female-type feature into which the proximal end of the fastener or fixation element inserts or locates in order to secure and/or center the fastener or fixation element against the piston. In some embodiments, the tension of the compressed or loaded spring builds up proximal to the piston in order to propel said piston in a distal direction when the triggering mechanism is actuated. In further embodiments, the piston comprises a retainer mechanism that prevents the piston from exiting the distal end of the barrel. In other embodiments, the piston is shaped such that the distal-most portion thereof protrudes from the barrel upon delivery of the fastener or fixation element into bone. In other particular embodiments, the device comprising a compressed or loaded spring lacks a piston, wherein the fastener or fixation element fits into the barrel in such a manner that the compressed or loaded spring is in contact with and proximal to the fastener or fixation element. Upon actuation of the triggering mechanism releasing the spring, said compressed or loaded spring drives said fastener or fixation element in a proximal to distal direction down the barrel into bone.

In another embodiment of the device, the device comprises a stretched elastic element and the contraction of said elastic element is the propellant for driving said at least one fastener or fixation element through said barrel into bone. In particular embodiments, the device comprising a stretched elastic element further comprises a piston for propelling a fastener or fixation element from the chamber, through the barrel from the proximal to the distal end and into the bone. In some embodiments, the piston has a proximal and a distal end and the distal end comprises a concave depression, cup, slot or other female-type feature into which the proximal end of the fastener or fixation element inserts or locates in order to secure and/or center the fastener or fixation element against the piston. In some embodiments, the tension of the stretched elastic element builds up proximal to the piston in order to propel said piston in a distal direction when the triggering mechanism is actuated. In further embodiments, the piston comprises a retainer mechanism that prevents the piston from exiting the distal end of the barrel. In other embodiments, the piston is shaped such that the distal-most portion thereof protrudes from the barrel upon delivery of the fastener or fixation element into bone. In other particular embodiments, the device comprising stretched elastic element lacks a piston, wherein the fastener or fixation element fits into the barrel in such a manner that the stretched elastic element is in contact with and proximal to the fastener or fixation element. Upon actuation of the triggering mechanism, said stretched elastic element drives said fastener or fixation element in a proximal to distal direction down the barrel into bone.

In still another embodiment of the device, the device comprises a friction mechanism for driving a fastener or fixation device in a proximal to distal direction down the barrel and into bone. In some embodiments, said friction mechanism comprises at least one wheel that contacts the side of said fastener or fixation device, wherein rotation of said at least one wheel drives said fastener or fixation device in a proximal to distal direction down the barrel and into bone. In some embodiments, the device comprises two wheels that are opposite one another, gripping said fastener or fixation device between them. In some embodiments, the at least one wheel is made from a flexible material including, but not limited to, silicon, rubber, latex, plastic or a combination thereof, including embodiments wherein one material is layered upon another material. In some embodiments, the at least one wheel is made of a rigid material, such as, but not limited to metal alloys, plastic or ceramic. In some embodiments, the at least one wheel is made from a rigid material coated with a flexible material. In other embodiments, the at least one wheel is made of a rigid material and is toothed, wherein the teeth grip notches in the sides of a fastener or fixation device.

In yet another embodiment of the device, the device comprises a cam and lever system for propelling at least one fastener or fixation element from the device into bone.

In some embodiments, said triggering mechanism comprises a means for regulating the propulsion source. For example, in some embodiments thereof, regulating the pressure of the gas charging said chamber. In other embodiments thereof, the triggering mechanism regulates the amount of compression of the spring. In still other embodiments thereof, the triggering mechanism regulates the amount of contraction of the elastic element.

In yet another embodiment, said trigger mechanism comprises a safety. In some further embodiments, said safety prevents charging said chamber with gas when the distal end of said barrel is not in contact with bone. In some further embodiments, said safety mechanism prevents actuation of the trigger mechanism when the distal end of said barrel is not in contact with bone.

In some embodiments, the barrel is interchangeable. For example, in some procedures, several different diameters, sizes or types of fasteners or fixation elements may be needed. In order to facilitate delivery of said different fasteners or fixation elements, barrels specific for a particular type of fastener or fixation element can be inserted into or removed from the device. For example, a barrel specific for the delivery of a K-wire may be initially installed in the device, such that a K-wire can be driven into bone. Subsequently, suture anchors may be needed for the attachment of tendon. Accordingly, the practitioner can remove the K-wire specific barrel from the device and replace it with a barrel specific for a suture anchor of the desired size. In some embodiments, the interchangeable barrels for the device are disposable.

In some embodiments, the device comprises an openable breach proximal to the barrel. Said openable breach allows the direct loading of at least one fastener or fixation element into the chamber or barrel. In some embodiments, the interchangeable barrel is installed into or removed from the device through the openable breach.

In some embodiments, an implanting device of the present application is sterilizable. In other embodiments, an implanting device of the present application is disposable.

Another aspect of the present application relates to a method for the fixation of a fractured bone using the implanting device of the application.

In one embodiment, the method comprises fixation of bone fragments of a long bone using an IM nail. The method comprises the steps of: providing an access point to the medullary canal of said long bone, reducing the bone fragments at the fracture, aligning the implanting device with said medullary canal at said access point, and actuating the trigger mechanism of said implanting device to deliver an IM nail into said medullary canal, thereby fixing said bone fragments in said reduced state. In some embodiments, said access point is percutaneous. In other embodiments, said access point is open.

In a further embodiment, said access point is a hole in the bone. In a still further embodiment, said hole is created with a drill. In another still further embodiment, said hole is created with an awl.

In another further embodiment, said long bone is selected from the group consisting of metatarsal bones and metacarpal bones, wherein said metatarsal bones and metacarpal bones include the phalanges.

In another embodiment, the method comprises fixation of bone fragments of a bone using at least one k-wire. The method comprises the steps of reducing at least one bone fragment with at least one adjacent fragment or the main body of the bone, aligning the implanting device with said at least one bone fragment and said at least one adjacent fragment or the main body of the bone, and actuating the trigger mechanism of said implanting device to deliver a k-wire affixing said at least one bone fragment to said at least one adjacent fragment or the main body of the bone, thereby fixing said at least one bone fragment in said reduced state.

In a further embodiment, said bone is the humerus. In a still further embodiment, said at least one bone fragment is from the proximal end of the humerus.

In another further embodiment, said bone is the femur. In a still further embodiment, said at least one bone fragment is from the head of the femur.

In yet another further embodiment, said bone is a carpal bone or a tarsal bone.

In some further embodiments, the method comprises fixing two or more bones together to facilitate healing of ligaments. In some embodiments, the two or more bones are carpal bones or tarsal bones.

In some embodiments, the proximal end of the K-wire is left protruding from the bone. In a further embodiment, a cross-pin fixation device is attached to the protruding proximal ends of the K-wires for further reduction or stabilization of the fracture.

Another aspect of the present application relates to a kit comprising an implantation device of the present application and a fastener or fixation element.

In one embodiment, the fastener or fixation element is selected from the group consisting of a k-wire, an IM nail, bone screw and a suture anchor. In some embodiments, the kit further comprises a biocompatible filler or adhesive material.

In another embodiment, the kit further comprises a replaceable cartridge for containing said at least one fastener or fixation element in said chamber. In a further embodiment, said cartridge is disposable. In another further embodiment, said cartridge contains more than one fastener or fixation element.

In another embodiment, said implantation device is pneumatic. In a further embodiment, said kit further comprises a propellant cartridge. In some embodiments, the propellant is compressed air.

FIG. 1 is a schematic view of one embodiment of the implanting device 100. In some embodiments, the implanting device 100 is sterilizable. In other embodiments, the implanting device 100 is disposable.

The implanting device 100 comprises a barrel 110 for propelling the fastener or fixation element into the bone, which is placed in contact with, or in proximity to, the distal end 115 of the barrel 110. The device further comprises a chamber 120 which holds the fastener or fixation element.

In some embodiments, the fastener or fixation element is held within a replaceable cartridge that is inserted into the chamber 120. In some embodiments, the cartridge holds a single fastener or fixation element. In other embodiments, the cartridge holds multiple fasteners or fixation elements. In particular embodiments, the cartridge is disposable.

In some embodiments, the device is adapted to be used with a single type of fastener or fixation device. In other embodiments, the device is usable with multiple types fasteners or fixation devices. In further embodiments, the fasteners or fixation devices include, but are not limited to k-wires, IM nails, screws and suture anchors.

In particular embodiments, the fasteners or fixation elements, or the cartridge that holds fasteners or fixation elements, is inserted into the implanting device 100 through an access panel 130 at the proximal end 135 of the implanting device 100.

Pressure for propelling a fastener or fixation element down the barrel 110 of the implanting device 100 is provided through a fitting 140 that is affixed to the chamber 120. In some embodiments, the fitting 140 comprises a tube. In other embodiments, the fitting 140 comprises a coupling for attaching to a gas source that provides a medically acceptable propellant gas. In still other embodiments, the fitting 140 comprises both a tube and a coupling.

In some embodiments, the gas source is an external source. In other embodiments, the gas source is a replaceable gas cartridge 150. In some embodiments, the replaceable gas cartridge 150 is insertable into the handle 160 of the implanting device 100. In some embodiments, the replaceable gas cartridge 150 is insertable through a port in the end 165 of the handle 160 in other embodiments, the replaceable gas cartridge 150 is insertable into a socket in the side or back of the handle 160.

In some embodiments, the medically acceptable propellant gas is medical grade compressed air. In still other embodiments, the medically acceptable propellant gas comprises nitrogen, oxygen or carbon dioxide. In some embodiments the replaceable gas cartridge 150 is reusable. In other embodiments, the replaceable gas cartridge 150 is disposable.

The chamber 120 is charged with propellant gas from the fitting 140 by actuation of a trigger mechanism 170. Actuation of the trigger mechanism 170 allows the propellant gas to propel a fastener or fixation element down the barrel 110 and into the bone that is in contact with, or in proximity to, the distal end 115 of the barrel 110.

In some embodiments, the trigger mechanism 170 further comprises a control element for adjusting the pressure of the propellant gas that is released into the chamber 120.

Also, in some embodiments, the implanting device 100 comprises a safety mechanism such that the distal end of the barrel 115 must be in contact with tissue in order for the implanting device 100 to operate. In some embodiments, unless the distal end of the barrel 115 is in contact with tissue, the trigger mechanism 170 cannot be actuated. In other embodiments, unless the distal end of the barrel 115 is in contact with tissue, the trigger mechanism 170 can be actuated, but the chamber 120 is not charged with propellant gas from the fitting 140.

In some other embodiments, the power for propelling a fastener or fixation element down the barrel of the implanting device 100 is provided by a mechanical device such as a spring, an electrical device such as a battery powered piston, or through a controlled explosion like in a firearm.

The present application is further illustrated by the following examples which should not be construed as limiting. The contents of all references, patents and published patent applications cited throughout this application, as well as the Figures and Tables, are incorporated herein by reference.

Example 1: Reduction and Fixation of Fractured Metacarpal Bone

A male subject presents with a fracture near the distal end of the second metacarpal bone on the left hand. The hand is x-rayed and the nature of the fracture indicates implantation of a bioabsorbable IM nail as the desired therapeutic approach.

The metacarpophalangeal joint is flexed 90 degrees exposing the metacarpal head, allowing direct access by the fixation device. The fracture is reduced and held in place and the trigger mechanism of the fixation device is actuated, firing the IM nail through the metacarpal head into the medullary canal of the phalanx, immobilizing the reduced fragments of the metacarpal in the correct position to allow union of the fragments at the fracture. The excess wire protruding is pulled out 4 mm proximally and trimmed and then tapped in all the way underneath the subchondral bone.

Example 2: Reduction and Fixation of Fractured Patella

A male subject presents with a fractured left patella. The knee is x-rayed and it is found that the patella is broken transversely into upper and lower fragments. The decision is made to reduce the fracture and immobilize the fragments with k-wires using a tension band procedure.

Briefly, a longitudinal incision is made over the patella and the patella is exposed. The fracture is reduced and held in place with a tenaculum having the pincers contacting the top and bottom of the patella along the centerline.

The implanting device, loaded with a cartridge comprising 2 mm diameter k-wires is contacted with the top of the patella and to one side of the tenaculum pincer. The implanting device is aimed to fire through both fragments of the patella such that the distal end of a first k-wire will protrude through the bottom of the patella. The trigger mechanism is actuated, forcing the first k-wire through the patella. The implanting device is moved to the top edge of the patella on the other side of the tenaculum pincer and a second k-wire is driven through the patella, parallel to the first.

A thin k-wire is passed behind the proximal ends of the 2 mm k-wires protruding from the top of the patella. The two ends of the thin k-wire are crossed over one another in front of the patella and one end is passed behind the distal ends of the 2 mm k-wires protruding from the bottom of the patella. The two ends of the thin wire are brought together in front of the patella and twisted together until completely taut. The distal ends of the 2 mm k-wires are trimmed and bent over the thin k-wire to secure it. The proximal ends of the 2 mm k-wires are also trimmed and soft tissue caps are placed over them. The incision over the patella is sutured closed.

The above description is for the purpose of teaching the person of ordinary skill in the art how to practice the present application, and it is not intended to detail all those obvious modifications and variations of it which will become apparent to the skilled worker upon reading the description. It is intended, however, that all such obvious modifications and variations be included within the scope of the present application, which is defined by the following claims. The claims are intended to cover the components and steps in any sequence which is effective to meet the objectives there intended, unless the context specifically indicates the contrary.

What is claimed is:

1. An implanting device for driving a fastener or fixation element into bone, comprising:
   a chamber for holding at least one fastener or fixation element,
   a barrel having a proximal end and a distal end, wherein said proximal end is connected to said chamber for propelling said fastener or fixation element from said chamber,
   a propellant source functionally connected to said chamber, and
   a mechanism for releasing propellant from said propellant source into said chamber and charging said chamber in order to propel said fastener or fixation element from said chamber through said barrel and driving said fastener or fixation element into bone contacted with said distal end, wherein said propellant directly engages said fastener or fixation element to drive the fastener or fixation element without the use of a piston.

2. The device of claim 1, wherein said fastener or fixation element is selected from the group consisting of a Kirschner wire, an intramedullary nail or a suture anchor.

3. The device of claim 1, further comprising a replaceable cartridge for containing said at least one fastener or fixation element in said chamber.

4. The device of claim 3, wherein said cartridge contains more than one fastener or fixation element.

5. The device of claim 1, wherein said propellant source is a tube that connects to an external gas supply.

6. The device of claim 1, wherein said propellant source is a replaceable canister of compressed gas.

7. The device of claim 1, wherein said mechanism for releasing propellant comprises a means for regulating the pressure of the propellant charging said chamber.

8. The device of claim 1, wherein said mechanism for releasing propellant comprises a safety mechanism that prevents charging said chamber with the propellant when the distal end of said barrel is not in contact with bone.

9. The device of claim 8, wherein said safety mechanism prevents actuation of the trigger mechanism when the distal end of said barrel is not in contact with bone.

10. A method for the fixation of a fractured long bone with an intramedullary nail, comprising:
    providing an access point to the medullary canal of said long bone,
    reducing the bone fragments at the fracture,
    contacting the distal end of the barrel of the pneumatic implanting device of claim 1 with said access point,
    aligning the barrel of said device with said medullary canal at said access point, and
    actuating the mechanism for releasing propellant of said implanting device to deliver an intramedullary nail into said medullary canal, thereby fixing said bone fragments in said reduced state.

11. The method of claim 10, wherein said access point is a hole in the bone.

12. The method of claim 11, wherein said hole is created with a drill.

13. The method of claim 11, wherein said hole is created with an awl.

14. The method of claim 10, wherein said long bone is selected from the group consisting of metatarsal bones and metacarpal bones.

15. The method of claim 14, wherein said metatarsal bones and metacarpal bones include the phalanges.

16. A method for the fixation a fractured bone using at least one Kirschner wire, comprising:
   reducing at least one bone fragment with at least one adjacent fragment or the main body of the bone,
   contacting the distal end of the barrel of the pneumatic implanting device of claim 1 with said at least one bone fragment, said at least one adjacent fragment or said main body of the bone,
   aligning the implanting device with said at least one bone fragment and said at least one adjacent fragment or said main body of the bone,
   and actuating the mechanism for releasing propellant of said implanting device to deliver a Kirschner wire affixing said at least one bone fragment to said at least one adjacent fragment or the main body of the bone, thereby fixing said at least one bone fragment in said reduced state.

17. The method of claim 16, wherein said bone is the humerus.

18. The method of claim 17, wherein said at least one bone fragment is from the proximal end of the humerus.

19. The method of claim 16, wherein said bone is the femur.

20. The method of claim 19, wherein said at least one bone fragment is from the head of the femur.

21. The method of claim 16, wherein said bone is a carpal bone or a tarsal bone.

22. A kit comprising the implantation device of claim 1 and a fastener or fixation element.

23. The kit of claim 22, wherein said fastener or fixation element is selected from the group consisting of a Kirschner wire, an intramedullary nail and a suture anchor.

24. The kit of claim 22, further comprising a replaceable cartridge for containing said at least one fastener or fixation element in said chamber.

25. The kit of claim 24, wherein said cartridge contains more than one fastener or fixation element.

26. The kit of claim 22, wherein said implantation device is a pneumatic implantation device.

27. The kit of claim 26, wherein said kit further comprises a propellant cartridge.

* * * * *